United States Patent [19]

Rose et al.

[11] Patent Number: 4,859,206

[45] Date of Patent: * Aug. 22, 1989

[54] HAIR DYE PREPARATIONS CONTAINING NITRODIPHENYLAMINE DERIVATIVE

[75] Inventors: David Rose, Hilden; Edgar Lieske, Duesseldorf; Horst Hoeffkes, Duesseldorf-Hellerhof; Norbert Maak, Neuss, all of Fed. Rep. of Germany

[73] Assignee: Henkel Kommanditgesellschaft auf Aktien, Duesseldorf, Fed. Rep. of Germany

[ * ] Notice: The portion of the term of this patent subsequent to Jul. 12, 2005 has been disclaimed.

[21] Appl. No.: 160,964

[22] Filed: Feb. 26, 1988

[30] Foreign Application Priority Data

Feb. 26, 1987 [DE] Fed. Rep. of Germany ....... 3706225

[51] Int. Cl.$^4$ .......................... A61K 7/13; C07C 87/54
[52] U.S. Cl. ............................................ 8/429; 8/407; 8/409; 8/414; 8/423; 544/166; 544/167; 544/392; 546/232; 548/550; 562/433; 562/434; 562/435; 562/61; 564/433; 564/434
[58] Field of Search ................... 8/429, 407, 423, 405, 8/414; 564/433, 434; 260/508, 509, 510, 515 C; 562/433, 434, 435; 544/166, 167, 392; 546/232; 548/550

[56] References Cited

U.S. PATENT DOCUMENTS

| 4,254,054 | 3/1981 | Arndt et al. | 260/510 |
| 4,494,953 | 1/1985 | Bugaut et al. | 8/408 |
| 4,698,066 | 10/1987 | Rose et al. | 8/410 |
| 4,756,716 | 7/1988 | Rose et al. | 8/429 |

FOREIGN PATENT DOCUMENTS 955743  4/1964  United Kingdom ................ 564/434
1517105 7/1978 United Kingdom .

OTHER PUBLICATIONS

J. Prakt. Chem. (2) 91, pp. 205–206, 210–211 (1915).
Beilsteins Handbuch der Organischen Chemie, F. Richter, Berlin, Germany, 1933, p. 564.
Chem. Abs. No. 85:79651z (Sep. 1976).
Chem. Abs. No. 84:126644r (May 1976).

Primary Examiner—Paul Lieberman
Assistant Examiner—Linda D. Skaling
Attorney, Agent, or Firm—Ernest G. Szoke; Wayne C. Jaeschke; Norvell E. Wisdom

[57] ABSTRACT

This invention encompasses compounds of the formula

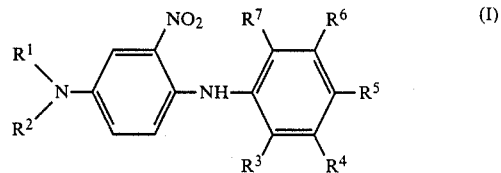

wherein $R^1$ and $R^2$ independently are hydrogen, $C_{1-4}$ alkyl, or $C_{2-4}$ hydroxyalkyl; one of $R^3$ to $R^7$ is —$SO_3H$ or —COOH; and the remaining of $R^3$ to $R^7$ independently are hydrogen, chlorine, $C_{1-4}$ alkyl, $C_{1-4}$ alkoxy, or —$NR^8R^9$, where $R^8$ and $R^9$ independently are hydrogen, $C_{1-4}$ alkyl, $C_{2-4}$ alkoxy, or where —$NR^8R^9$ is piperidine, morpholine, piperazine, or pyrrolidone; or a water soluble salt thereof; hair dye preparation containing these compounds, and methods for dyeing hair using such preparation.

34 Claims, No Drawings

HAIR DYE PREPARATIONS CONTAINING NITRODIPHENYLAMINE DERIVATIVE

BACKGROUND OF THE INVENTION

1. Field of the Invention

This invention relates to hair dye preparations containing substantive hair dyes as well as some of the dyes per se. Preparations of the type in question contain substantive hair dyes in a cosmetic carrier. In many cases, such preparations additionally contain oxidation dye precursors to produce certain shades. The cosmetic carriers used for the substantive hair dyes and oxidation dye precursors, if any, are creams, emulsions, gels, shampoos, foam aerosols or other preparations suitable for application to the hair.

2. Statement of Related Art

In addition to the oxidation dyes, which are formed by the oxidative coupling of one or more developer components with one or more coupler components, substantive hair dyes play a prominent part in the dyeing of hair. Substantive dyes have the advantage of being used without the addition of oxidizing agents. The substantive dyes used are predominantly nitrobenzene derivatives. They are used either on their own or in combination with other substantive dyes, cationic azo dyes such as anthraquinone dyes, indophenols, triphenylmethane dyes, or with oxidation dyes.

Good hair-dyeing preparations have to form the required shades with sufficient intensity. They must be readily absorbed by human hair without excessively staining the scalp. The coloring produced with them must show high stability to light, heat, perspiration, shampoos and the chemicals used in the permanent waving of hair. Finally, they should be safe to use from the toxicological and dermatological viewpoint.

Among the substantive nitrobenzene derivatives, the nitroanilines and derivatives thereof play an important part because some of these dyes produce intensive, light-stable colors. However, the known substantive nitroaniline dyes have disadvantages in that, on the one hand, they show only limited solubility in water, which leads to problems during formulation of the hair dye preparations, and on the other hand they are not sufficiently fast to washing, i.e. the dye finishes fade considerably after repeated shampooing.

In addition, it is desirable that substantive dyes should be able to produce shades of red to obtain fashionable hair colors. 2-Nitro-p-phenylenediamine and amino-substituted derivatives thereof are normally used for this purpose. Unfortunately, these chemically related compounds are difficult to dissolve and difficult to disperse in water. This readily leads to uneven or to faint hair colors. Moreover, particularly where hair preparations have high concentrations of dye, the dyes crystallize out and are not adsorbed onto the hair to be dyed. Accordingly, there is an urgent need for substantive hair dyes showing improved solubility in water.

Furthermore, substantive hair dyes desireably show high compatibility with other dyes, for example with oxidation dye precursors and with the other components normally used in oxidation hair dye preparations, because substantive dyes and oxidation dyes are often combined with one another for color modification. Accordingly, high stability to reducing agents and oxidizing agents is necessary.

DESCRIPTION OF THE INVENTION

Other than in the operating examples, or where otherwise indicated, all numbers expressing quantities of ingredients or reaction conditions used herein are to be understood as modified in all instances by the term "about".

This invention provides hair dye preparations containing one or more substantive hair dyes, in an aqueous cosmetic carrier, in which the substantive hair dyes are one or more compounds of the formula:

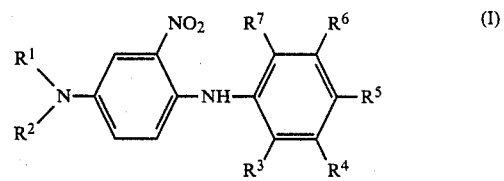

wherein: $R^1$ and $R^2$ independently are hydrogen, $C_{1-4}$ alkyl or $C_2$-hydroxyalkyl; one of the substituents $R^3$ to $R^7$ is —SO₃H or —COOH; and the other substituents independently are hydrogen, chlorine, $C_{1-4}$ alkyl, $C_{1-4}$ alkoxy, or —NR⁸R⁹, where $R^8$ and $R^9$ are independently hydrogen, $C_{1-4}$ alkyl, $C_{2-4}$ hydroxyalkyl or, together with the —NR⁸R⁹ nitrogen atom, form a piperidine, morpholine, piperazine or pyrrolidone ring, and water soluble salts thereof.

Preferred compounds of formula (I) are those in which one of the substituents $R^3$ and $R^7$ is COOH or —SO₃H and at least two of the other substituents are hydrogen.

Compounds in which (a) one of the substituents $R^3$ to $R^7$ is COOH or SO₃H and all of the other substituents are hydrogen, or (b) one of the other substituents is chlorine, methyl, methoxy or —NR⁸R⁹ where $R^8$ and $R^9$ are not both hydrogen, and the other substituents are hydrogen, are particularly preferred by virtue of their ready technical accessibility.

The dyes corresponding to formula (I) produce deep yellow, brown, red and blue shades of high intensity and fastness to light and shampooing of the hair. Compared with those isomers in which the position of the —NR¹R² or NO₂ moiety is changed, the nitrophenylenediamine derivatives according to the invention show distinctly increased fastness to light.

The compounds corresponding to formula (I) are novel, so that this invention also includes these compounds per se.

In general, the compounds corresponding to formula (I) are prepared by the reaction of 4-fluoro-3-nitroanilines corresponding to the formula

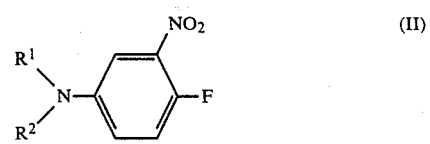

with an aminobenzenesulfonic acid or aminobenzoic acid corresponding to the formula

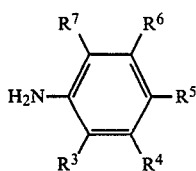

(III)

with elimination of HF in the presence of a base, for example an alkali carbonate, the groups $R^1$ to $R^7$ in formulae (II) and (III) being as defined for formula (I).

In the context of the invention, water soluble salts are primarily understood to be the salts of strong bases, including: alkali salts, such as sodium or potassium, ammonium salts, $C_{2-4}$ alkanolammonium salts such as monoethanolammonium, triethanolammonium, or isopropanolammonium, sodium being preferred.

The hair dye preparations according to the invention may contain the (first) substantive nitrodiphenylamine derivatives corresponding to formula (I) either alone or in combination with known other (second) substantive dyes, for example with other nitrobenzene derivatives, anthraquinone dyes, triphenylmethane dyes or azo dyes. When present, the second substantive hair dyes are in any amount effective to alter the color of hair to be treated to a desired degree. In a further invention embodiment, the substantive dyes of general formula (I), by virtue of their high resistance to reducing agents and oxidizing agents, are also eminently suitable for combination with oxidation dye precursors, i.e. for modifying the shades of oxidation hair dye preparations. Oxidation hair dye preparations contain as dye precursors developer components which form the oxidation dyes by oxidative coupling with one another or with suitable coupler components. Suitable developer components useful in this invention include primary aromatic amines containing another free or substituted hydroxy or amino moiety in the para or ortho position, diaminopyridine derivatives, heterocyclic hydrazones, 4-aminopyrazolone derivatives and 2,4,5,6-tetraaminopyrimidine and derivatives thereof. Suitable coupler components useful in this invention include m-phenylenediamine derivatives, naphthols, resorcinol and resorcinol derivatives, pyrazolones and m-aminophenols. The couplers and developers, when present, are in oxidative hair dye effective amounts in relation to each other. The combined oxidative hair dye precursors, with the required oxidizing agent present in an oxidizing agent effective amount, may be present in any amount effective to alter the color of hair to be treated, to a desired degree.

To produce the hair dye preparations according to the invention, the first and optional second substantive hair dyes and the optional oxidation dye precursors, if any, are incorporated in suitable cosmetic carriers, such as creams, emulsions, gels, surfactant-containing foaming solutions such as shampoos, foam aerosols, or other preparations which are suitable for application to the hair.

Standard constituents of cosmetic preparations such as the above include: wetting agents and emulsifiers such as anionic, nonionic or ampholytic surfactants, preferably fatty alcohol sulfates, alkanesulfonates, alpha-olefin sulfonates, fatty alcohol polyglycol ether sulfates, ethylene oxide adducts with fatty alcohols, fatty acid adducts with alkylphenols, sorbitan fatty acid esters and fatty acid partial glycerides, and fatty acid alkanolamides; thickeners such as methyl or hydroxyethyl cellulose, starch, fatty alcohols, paraffin oils, and fatty acids; and perfume oils and hair-care additives such as water soluble cationic polymers, protein derivatives, pantothenic acid and cholesterol. The constituents of the cosmetic carriers are used in the usual quantities effective for preparing the hair dye preparations according to the invention. For example, emulsifiers are used in concentrations of 0.5 to 30% by weight and thickeners in concentrations of 0.1 to 25% by weight.

In the hair dye preparations according to the invention, the substantive hair dyes corresponding to general formula (I) preferably are used in a quantity of from 0.01 to 5.0% by weight, most preferably 0.1 to 2% by weight. In addition, known oxidation hair dye precursors (developer and coupler components, etc.) preferably are present in a combined quantity of from 0.01 to 5.0% by weight, most preferably 1.0 to 3.0% by weight.

If the hair dye preparation according to the invention contains oxidation dye precursors, it also is advisable to add a small quantity of a reducing agent, for example from 0.5 to 2.0% by weight of sodium sulfite, to stabilize the oxidation dye precursors. In this case, an oxidizing agent is added to the hair dye preparation before use in order to initiate oxidative development of the oxidation dye precursors. Oxidizing agents useful in this invention include, in particular, hydrogen peroxide or adducts thereof with urea, melamine or sodium borate as well as mixtures of these hydrogen peroxide adducts with potassium peroxysulfate. All of the above weights are based upon the weight of the hair dye preparation as a whole, it being understood that water is employed q.s. to 100%.

The hair dye preparations according to the invention may be used in a mildly acidic, neutral or alkaline medium, irrespective of the cosmetic carrier used, for example a cream, gel or shampoo. The hair dye preparations preferably have a pH range from 8 to 10. They may be used at temperatures of from 15° to 40° C. After a contact time of around 30 minutes, the hair dye preparation is removed by rinsing from the hair to be dyed. The hair may then be washed with a mild shampoo and dried. Washing with a shampoo is unnecessary when a carrier of high surfactant content, for example a dye shampoo, is used.

Hair dye finishes of high intensity, good fastness properties particularly to shampooing, and high stability to bleeding and changes in color during shampooing may be obtained with the hair dye preparations according to the invention. The following Examples are intended to illustrate the invention without limiting it in any way.

EXAMPLES

Preparation Examples 1. 2-nitro-4-aminodiphenylamine-2'-carboxylic acid

A mixture of (A) 27.4 g (0.2 mol) anthranilic acid, (B) 31.2 g (0.2 mol) 4-fluoro-3-nitroaniline, 27.6 g (0.2 mol) potassium carbonate and approx. 0.1 g copper powder was heated to approximately 130° C. After a reaction time of 3 hours at that temperature, the mixture was cooled and thoroughly boiled with 200 ml water. After undissolved fractions had been filtered off, the hot (80° C.) aqueous solution was adjusted to pH 3 with dilute hydrochloric acid.

The red deposit was filtered off and dried.

Yield: red crystals, melting point approx. 212° C. (with decomposition)

2. 2-nitro-4-N,N-bis(2-hydroxyethyl)-aminodiphenylamine-2'-carboxylic acid

Prepared as in Example 1 from
(A) anthranilic acid and
(B) 4-fluoro-3-nitro-N,N,-bis(2-hydroxyethyl)-aminobenzene Yield: red crystals, melting point approx. 70° C. (with decomposition)

3. 2-nitro-4-amino-4'-chlorodiphenylamine-2'-carboxylic acid

Prepared as in Example 1 from
(A) 2-amino-5-chlorobenzoic acid and
(B) 4-fluoro-3-nitroaniline Yield: dark red powder, melting point 284° C. (with decomposition).

4. 2-nitro-4-amino-4'-methyldiphenylamine-2'-carboxylic acid

Prepared as in Example 1 from
(A) 2-amino-5-methylbenzoic acid and
(B) 4-fluoro-3-nitroaniline Yield: brown-red powder, melting point 257° C. to 263° C.

5. 2-nitro-4-amino-5'-chlorodiphenylamine-2'-carboxylic acid

Prepared as in Example 1 from
(A) 2-amino-4-chlorobenzoic acid
(B) 4-fluoro-3-nitroaniline Yield: red-brown powder, melting point approx. 260° C. (with decomposition)

6. 2-nitro-4-N,N-bis-(2-hydroxyethyl)-aminodiphenylamine-4'-carboxylic acid, potassium salt A mixture of (A) 3.4 g (0.025 mol) 4-aminobenzoic acid, (B) 6.2 g (0.025 mol) 4-fluoro-3-nitro-N,N-bis-(2-hydroxyethyl)-aminobenzene, 3.8 g (0.027 mol) potassium carbonate and 10 ml water was heated for 7 hours to 120° C. in an autoclave. After cooling, the solution was concentrated to dryness. The residue was recrystallized from a mixture of ethanol and water.

Yield: red crystals, melting point above 250° C.

7. 2-nitro-4-aminodiphenylamine-3'-sulfonic acid

Prepared as in Example 1 from
(A) 3-aminobenzenesulfonic acid and
(B) 4-fluoro-3-nitroaniline Yield: brown crystals, melting point beyond approx. 285° C. (with decomposition)

8. 2-nitro-4-dimethylaminodiphenylamine-3'-sulfonic acid, potassium salt

Prepared as in Example 6 from
(A) 3-aminobenzene sulfonic acid and
(B) N,N-dimethyl-3-nitro-4-fluoroaniline Yield: violet powder, UV spectrum (pH=9.5); max—486 nm 9. 2-nitro-4-amino-4'-methoxydiphenylamine-2'-carboxylic acid Prepared as in Example 6 from
(A) 5-methoxy-2-aminobenzoic acid and
(B) 4-fluoro-3-nitroaniline Yield: violet crystals, melting point 202° C. (with decomposition)

10. 2-nitro-4-amino-4'-dimethylaminodiphenylamine-2'-carboxylic acid

Prepared as in Example 1 from
(A) 5-dimethylamino-2-aminobenzoic acid from 5-dimethylamino-2-nitrobenzoic acid by catalytic hydrogenation over Pol (carbon in ethanol at 25° C.; white powder melting at 213° C. and
(B) 4-fluoro-3-nitroaniline Yield: black powder, melting point 180°-190° C.

11. 2-nitro-4-amino-6'-methoxydiphenylamine-2'-carboxylic acid

Prepared as in Example 1 from
(A) 2-amino-3-methoxybenzoic acid and
(B) 4-fluoro-3-nitroaniline Yield: dark red powder, melting point approx. 141° C. (decomposition)

12. 2-nitro-4-amino-4'-methoxydiphenylamine-2'-carboxylic acid

Prepared as in Example 1 from
(A) 2-amino-5-methoxybenzoic acid and
(B) 4-fluoro-3-nitroaniline Yield: red-violet powder, melting point 202°-242° C. (decomposition)

13. 2-nitro-4-amino-4'-(N,N-dimethylamino)-diphenylamine-3'-sulfonic acid

Prepared as in Example 1 from
(A) 2-dimethylamine-5-aminobenzenesulfonic acid and
(B) 4-fluoro-3-nitroaniline Yield: dark red powder, melting point above 300° C.

Hair dye tests of Examples 1 to 13

Hair dye creams were prepared from the following constituents:

| | |
|---|---|
| Fatty alcohol $C_{12-18}$ | 10 g |
| Fatty alcohol $C_{12-14}$ + 2 E.O. sulfate, Na salt (28%) | 25 g |
| Water | 60 g |
| Substantive dye according to fomula I | 1 g |
| Ammonium sulfate | 1 g |
| Concentrated ammonia solution | to pH 9.5 g |
| Water | q.s. ad 100 g |

The constituents were mixed together in the above order. After addition of the substantive dyes, the pH of the emulsion was first adjusted to 9.5 with concentrated ammonia solution, after which the emulsion was made up with water to 100 g.

The hair dye cream was applied to approximately 5 cm long strands of standardized, 90% grey, but not specially pre treated human hair and left thereon for 30 minutes at 27° C. After dyeing, the hair was rinsed, washed with a standard shampoo and then dried.

The compounds shown in Examples 1 to 13 were used as substantive hair dyes. The results of the dyeing tests are shown in the below Table.

TABLE

| Substantive dye of Example no. | Color of dyed hair |
|---|---|
| 1 | violet-brown |
| 2 | ruby |
| 3 | violet-brown |
| 4 | dark magenta |
| 5 | red brown |
| 6 | ruby |
| 7 | violet-brown |
| 8 | deep yellow |
| 9 | dark purple |
| 10 | indigo |
| 11 | grey-brown |
| 12 | dark purple |
| 13 | grey-red |

We claim:

1. In a hair dye aqueous preparation comprising a hair dye effective amount of a first substantive hair dye in a suitable cosmetic carrier including an amount of an anionic, nonionic or ampholytic surfactant effective as a wetting agent and emulsifier, the improvement wherein said first substantive hair dye comprises one or more compounds of the formula:

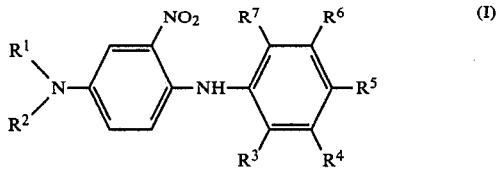

wherein:
$R^1$ and $R^2$ independently are hydrogen, $C_{1-4}$ alkyl, or $C_{2-4}$ hydroxyalkyl;
one of $R^3$ to $R^7$ is —$SO_3H$ or —COOH; and
the remaining of $R^3$ to $R^7$ independently are hydrogen, chlorine, $C_{1-4}$ alkyl, $C_{1-4}$ alkoxy, or —$NR^8R^9$, where $R^8$ and $R^9$ independently are hydrogen, $C_{1-4}$ alkyl, $C_{2-4}$ alkoxy, or where —$NR^8R^9$ is piperidine, morpholine, piperazine, or pyrrolidone;
or a water soluble salt thereof.

2. The hair dye preparation of claim 1 wherein in the formula, one of $R^3$ to $R^7$ is —$SO_3H$ or —COOH, and all of the remaining are hydrogen.

3. The hair dye preparation of claim 1 wherein in the formula: one or $R^3$ to $R^7$ is —$SO_3H$ or —COOH; one of $R^3$ to $R^7$ is chlorine, methyl, methoxy, or —$NR^8R^9$ where $R^8$ and $R^9$ are not both hydrogen; and all of the remaining are hydrogen.

4. The hair dye preparation of claim 1 wherein said first substantive hair dye is a water soluble salt of potassium, sodium, ammonium, or a $C_{2-4}$ alkanolammonium.

5. The hair dye preparation of claim 1 wherein said first substantive hair dye is 2-nitro-4-aminodiphenylamine-2'-carboxylic acid.

6. The hair dye preparation of claim 1 wherein said first substantive hair dye is 2-nitro-4-N,N-bis-(2-hydroxyethyl)-aminodiphenylamine-2'-carboxylic acid.

7. The hair dye preparation of claim 1 wherein said first substantive hair dye is 2-nitro-4-amino-4'-chlorodiphenylamine-2'-carboxylic acid.

8. The hair dye preparation of claim 1 wherein said first substantive hair dye is 2-nitro-4-amino-4'-methyldiphenylamine-2'-carboxylic acid.

9. The hair dye preparation of claim 1 wherein said first substantive hair dye is 2-nitro-4-amino-5'-chlorodiphenylamine-2'-carboxylic acid.

10. The hair dye preparation of claim 1 wherein said first substantive hair dye is 2-nitro-4-N,N-bis-(2-hydroxyethyl)-aminodiphenylamine-4'-carboxylic acid, potassium salt.

11. The hair dye preparation of claim 1 wherein said first substantive hair dye is 2-nitro-4-aminodiphenylamine-3'-sulfonic acid.

12. The hair dye preparation of claim 1 wherein said first substantive hair dye is 2-nitro-4-dimethylaminodiphenylamine-3'-sulfonic acid, potassium salt.

13. The hair dye preparation of claim 1 wherein said first substantive hair dye is 2-nitro-4-amino-4'-methoxydiphenylamine-2'-carboxylic acid.

14. The hair dye preparation of claim 1 wherein said first substantive hair dye is 2-nitro-4-amino-4'-dimethylaminodiphenylamine-2'-carboxylic acid.

15. The hair dye preparation of claim 1 wherein said first substantive hair dye is 2-nitro-4-amino-6'-methoxydiphenylamine-2'-carboxylic acid.

16. The hair dye preparation of claim 1 wherein said first substantive hair dye is 2-nitro-4-amino-4'-methoxydiphenylamine-2'-carboxylic acid.

17. The hair dye preparation of claim 1 wherein said first substantive hair dye is 2-nitro-4-amino-4'-(N,N-dimethylamino)-diphenylamine-3'-sulfonic acid.

18. The hair dye preparation of claim 1 in which said first substantive hair dye is present in about 0.01 to 5.0% by weight, based upon the weight of the hair dye as a whole.

19. The hair dye preparation of claim 1 wherein at least one substantive hair dye, at least one oxidative hair dye precursor, or mixtures thereof, is present in an amount effective to alter the color of hair to be treated to a desired degree.

20. The hair dye preparation of claim 1 wherein at least one oxidative hair dye precursor is present in a quantity of about 0.01 to 5.0% by weight, based upon the weight of the hair dye preparation as a whole.

21. The hair dye preparation of claim 1, formulated as a cream, an emulsion, a gel, a shampoo, or an aerosol foam.

22. The hair dye preparation of claim 19 formulated as a cream, an emulsion, a gel, a shampoo, or an aerosol foam.

23. A method for dyeing hair comprising
applying to the hair a hair-dyeing effective amount of the preparation of claim 1;
permitting said preparation to remain on said hair for a hair-dyeing effective time; and
removing said hair dye from said hair.

24. A nitrodiphenylamine derivative compound of the formula

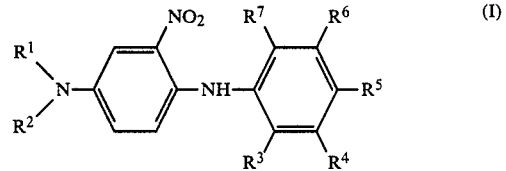

wherein:
$R^1$ and $R^2$ independently are hydrogen, $C_{1-4}$ alkyl, or $C_{2-4}$ hydroxyalkyl;
one of $R^3$ to $R^7$ is —$SO_3H$ or —COOH; and
the remaining of $R^3$ to $R^7$ independently are hydrogen, chlorine, $C_{1-4}$ alkyl, $C_{1-4}$ alkoxy, or —$NR^8R^9$, where $R^8$ and $R^9$ independently are hydrogen, $C_{1-4}$ alkyl, $C_{2-4}$ alkoxy, or where —$NR^8R^9$ is piperidine, morpholine, piperzine, or pyrrolidone; and when one of $R^3$ to $R^7$ is —COOH, then at least one of the remaining $R^3$ to $R^7$ is other than hydrogen;
or a water soluble salt thereof.

25. The compound of claim 24 having the formula 2-nitro-4-amino-4'-chlorodiphenylamine-2'-carboxylic acid.

26. The compound of claim 24 having the formula 2-nitro-4-amino-4'-methyl diphenylamine-2'-carboxylic acid.

27. The compound of claim 24 having the formula 2-nitro-4-amino-5'-chlorodiphenylamine-2'-carboxylic acid.

28. The compound of claim 24 having the formula 2-nitro-4-aminodiphenylamine-3'-sulfonic acid.

29. The compound of claim 24 having the formula 2-nitro-4-dimethylaminodiphenylamine-3'-sulfonic acid, potassium salt.

30. The compound of claim 24 having the formula 2-nitro-4-amino-4'-methoxydiphenylamine-2'-carboxylic acid.

31. The compound of claim 24 having the formula 2-nitro-4-amino-4'-dimethylaminodiphenylamine-2'-carboxylic acid.

32. The compound of claim 24 having the formula 2-nitro-4-amino-6'-methoxydiphenylamine-2'-carboxylic acid.

33. The compound of claim 24 having the formula 2-nitro-4-amino-4'-methoxydiphenylamine-2'-carboxylic acid.

34. The compound of claim 24 having the formula 2-nitro-4-amino-4'-(N,N-dimethylamino)-diphenylamine-3'-sulfonic acid.

* * * * *